(12) United States Patent
Bernstein

(10) Patent No.: US 8,604,047 B2
(45) Date of Patent: Dec. 10, 2013

(54) METHOD AND COMPOSITION FOR TREATING NODULOCYSTIC AND CONGLOBATE ACNE VULGARIS

(75) Inventor: Joel E. Bernstein, Deerfield, IL (US)

(73) Assignee: Elorac, Inc., Vernon Hills, IL (US)

( * ) Notice: Subject to any disclaimer, the term of this patent is extended or adjusted under 35 U.S.C. 154(b) by 290 days.

(21) Appl. No.: 12/854,033

(22) Filed: Aug. 10, 2010

(65) Prior Publication Data

US 2012/0041015 A1 Feb. 16, 2012

(51) Int. Cl.
*A61K 31/473* (2006.01)
*A61P 17/10* (2006.01)

(52) U.S. Cl.
USPC ........... 514/284; 514/859; 514/844; 514/852; 514/874; 514/880

(58) Field of Classification Search
USPC .................. 514/284, 859, 844, 852, 874, 880
See application file for complete search history.

(56) References Cited

U.S. PATENT DOCUMENTS 6,174,892 B1 * 1/2001 Gormley et al. .............. 514/284

OTHER PUBLICATIONS

Acne Science Article Jan. 2008 (Finasteride in Acne treatment, downloaded from the internet on Dec. 19, 2011, URL: http://web.archive.org/web/20080113210818/http://www.acnescience.com/acne-treatment/finasteride.shtml ).*
Acnenet article (Severe acne types, Aug. 2007, retrieved from the internet on Dec. 20, 2011, URl: http://web.archive.org/web/20070821210925/http://www.skincarephysicians.com/acnenet/severeacne4types.html.*

* cited by examiner

*Primary Examiner* — Savitha Rao
(74) *Attorney, Agent, or Firm* — Barnes & Thornburg LLP; Alice O. Martin

(57) ABSTRACT

Methods and compositions are described for the treatment of very severe acne vulgaris, including nodulocystic acne and conglobate acne. Compounds which inhibit either or both type 1 and type 2 isoforms of steroid 5α-reductase are administered daily in either oral or topical formulations to patients suffering from severe forms of acne vulgaris. Very high dosages of such compounds can effectively be administered oral just once a week and be successful.

6 Claims, No Drawings

METHOD AND COMPOSITION FOR TREATING NODULOCYSTIC AND CONGLOBATE ACNE VULGARIS

BACKGROUND

Acne vulgaris is a common self limited disorder of the pilosebaceous unit of the skin which usually is characterized by comedones, papules, pustules and nodules on the face, chest and back. Acne vulgaris affects both males and females. The greatest numbers of cases are seen in adolescents and teenagers. Most garden varieties of acne vulgaris are reasonably well treated and controlled with a variety of topical therapies as well as orally administered antibiotics. However, there are more uncommon severe acne variants that are much more difficult to treat. These are principally nodulocystic acne vulgaris and acne conglobata. Nodulocystic acne affects both males and females, and along with acne comedones, papules, and pustules, is accompanied by a number of inflammatory acne nodules and cysts. Acne conglobata (also known as conglobate acne) is the rare, but most severe form of acne, which is found predominately in males. In acne conglobata lesions usually occur on most of the face, trunk and limbs. Nodules are characteristic and frequently fuse to form multiple draining sinuses which may discharge a foul-smelling material. Healing results in extreme scarring, and acne conglobata is often much more persistent then other forms of acne. Treatment of these severe acne variants has been primarily limited to orally administered isotretinoin, but the popularity of this mode of therapy has significantly diminished of late due to a variety of serious systemic side effects associated with its usage. Consequently, there is a great medical need for a safe and effective treatment for these types of severe acne.

Over the last decade, agents which are selective inhibitors of either or both type 1 or type 2 isoforms of steroid 5α-reductase (5AR), an intracellular enzyme that converts testosterone to the much more potent 5α-dihydrotestosterone (DHT), have been widely utilized to treat symptomatic benign prostatic hyperplasia (BPH) in men with enlarged prostate glands. More recently the regular use of such selective inhibitors of 5AR has been advocated to prevent development of cancer of the prostate or to shrink aggressive prostatic tumors. These drugs have not been used in younger males.

SUMMARY OF THE DISCLOSURE

Methods and compositions are described for the treatment of very severe acne vulgaris, including nodulocystic acne and conglobate acne. Compounds which inhibit either or both type 1 and type 2 isoforms of steroid 5α-reductase are administered daily in either oral or topical formulations to patients suffering from severe forms of acne vulgaris. The oral dosage form is administered once or twice daily. Very high dosages of such compounds (≥20 mg) can effectively be administered orally just once a week and be successful.

Administration of daily oral or topical formulations containing agents which inhibit 5AR, including synthetic 4-azasteroid compounds such as finasteride and dutasteride, produced dramatic improvement in male patients with nodulocystic or conglobate acne.

A method of treating severe acne vulgaris including nodulocystic acne and acne conglobata includes administering oral dosages of selective inhibitors of type 1 and/or type 2 isoforms of steroid 5α-reductase to the affected subject. High dosages (≥20 mg/day) of the oral dosage form may be administered once weekly. Selective inhibitors are selected from the group consisting of the synthetic 4-azasteroid compounds finasteride, dutasteride, their salts and congeners. The inhibitors may be incorporated into formulations suitable for oral administration.

The synthetic 4-azasteroid compounds are administered orally in the range of from 0.05 mg to 80 mg by weight in each single dosage.

A method of treating severe acne of the nodulocystic or conglobate varieties, includes topically administering a therapeutically effective amount of a selective inhibitor of type 1 and/or type 2 isoforms of steroid 5α-reductase to a patient having nodulocystic or conglobate acne vulgaris.

A selective inhibitor of the isoforms of steroid 5α-reductase is a synthetic 4-azasteroid compound, particularly finasteride and dutasteride and their salts, congeners, and derivatives.

The synthetic 4-azasteroid compounds are present in topical formulations in the range of from about 0.01% to 20% by weight.

The topical formulation containing the selective inhibitor of isoforms of steroid 5α-reductase is applied by patients to involved skin 1-3 times daily.

A vehicle carrier is selected from the group consisting of creams, gels, lotions, solutions and ointments.

A topical composition for treating severe acne vulgaris, including nodulocystic acne and acne conglobata is a therapeutically effective amount of a selective inhibitor of isoforms of steroid 5α-reductase incorporated into pharmaceutically acceptable vehicles for application to the skin.

DETAILED DESCRIPTION OF THE DISCLOSURE

Surprisingly, methods and compositions for oral as well as topical administration of agents which inhibit 5AR can successfully treated patients with nodulocystic or conglobate acne. Useful 5AR inhibitors include synthetic 4-azasteroid compounds such as finasteride and dutasteride, as well as salts, congeners and derivatives of these compounds. Because these agents are teratogenic, they are most useful in treating severe nodulocystic or conglobate acne in adolescent, teenage and young adult males. Synthetic 4-azasteroid compounds are incorporated into tablets, capsules, caplets, suspensions and solutions for oral administration to patients with severe acne vulgaris. These oral dosage forms are then administered once or twice daily with or without food in single dosages of 0.05 mg-40 mg by weight of dutasteride or 0.05 mg-80 mg by weight of finasteride. Dosages of finasteride or dutasteride of ≥20 mg can be administered once a week and still maintain some efficacy.

Additionally, synthetic 4-azasteroid compounds are incorporated into solution, lotion, cream, ointment and gel formulations for application to the skin of patients with severe acne. In such topical formulations, concentrations from 0.01% to 20% by weight of finasteride, dutasteride or another 4-azasteroid compound are incorporated into vehicle suitable for application to the skin. The resulting formulations are applied to the skin of acne patients from 1 to 3 times daily.

Example 1

Tablets containing 0.5 mg by weight of finasteride are administered once daily for 12 weeks to patients with nodulocystic acne. At the end of the 12-week treatment period, most patients will demonstrate a significant decrease in the activity of their inflammatory acne lesions.

Example 2

Capsules containing 0.05 mg by weight of dutasteride are administered twice daily for 6 months to patients with conglobate acne. Patients will have resolution of some of their inflammatory nodules, cysts and sinus tracts by the end of the 6-month treatment period.

Example 3

Caplets containing 50 mg by weight of finasteride are administered once a week for 24 weeks to patients with severe nodulocystic acne. At the end of the 24-week treatment period, most patients demonstrate a marked reduction in acne nodules and cysts.

Example 4

A flavored oral solution incorporating a 0.75 mg by weight of dutasteride per every 5 ml of solution is administered to young patients with acne conglobata once daily for 24 weeks. At the end of treatment some patients will have complete resolution of their conglobate acne.

Example 5

Tablets containing 0.1 mg by weight of finasteride are administered once daily for 12 weeks to patients with acne conglobata. By the end of the treatment period, most patients will have very few new acne lesions and most of the old acne lesions will have resolved with only minor scarring.

Example 6

Patients with active nodulocystic acne apply 0.05% by weight finasteride prepared in an alcoholic gel containing 6% polyoxyethylene lauryl ether twice daily for 12 weeks. By the end of the treatment, patients will have fewer nodules and cysts then before starting treatment.

Example 7

A 5% dutasteride cream is prepared containing water, propylene glycol, bentonite, glycerol stearate, isopropyl myristate and cellulose gum, and applied once daily to the skin of patients with numerous acne papules, pustules, nodules and cysts for 8 weeks. After 8 weeks of such treatment, most patients will have at least a 20% decrease in the number of inflammatory acne lesions.

Example 8

An aqueous/alcohol solution containing 20% by weight finasteride is applied once daily by patients with nodulocystic acne. After two weeks of such treatment most patients will observe some improvement, and after twelve weeks of such therapy many patients will notice dramatic improvement in their appearance.

The invention claimed is:

1. A method of treating severe acne vulgaris, the method comprising administering oral dosages of selective inhibitors of type 1 and/or type 2 isoforms of steroid 5α-reductase once weekly at a dose of at least 20 mg.

2. The method of claim 1 wherein the selective inhibitors are selected from the group consisting of the synthetic 4-azasteroid compounds finasteride, dutasteride, their salts and congeners.

3. The method of claim 1 where severe acne vulgaris consists essentially of nodulocystic acne and acne conglobata.

4. The method of claim 1 wherein the inhibitors are incorporated into formulations suitable for oral administration.

5. The method of claim 2 wherein the synthetic 4-azasteroid compounds are present in the range of from 20 mg to 80 mg by weight in each single dosage.

6. The method of claim 5 wherein 20-80 mg of the oral dosage form is administered once weekly.

* * * * *